United States Patent [19]

Denton et al.

[11] Patent Number: 5,482,866

[45] Date of Patent: Jan. 9, 1996

[54] METHOD FOR QUANTITATION OF CALCIUM AND MAGNESIUM AND THE NOVEL REAGENT COMPOSITIONS

[75] Inventors: James B. Denton, Montclair; Diane J. Dixon; Richard A. Kaufman, both of Belleville, all of N.J.

[73] Assignee: Hoffmann-La Roche Inc., Nutley, N.J.

[21] Appl. No.: 281,808

[22] Filed: Jul. 28, 1994

Related U.S. Application Data

[63] Continuation of Ser. No. 996,361, Dec. 23, 1992, abandoned, which is a continuation of Ser. No. 765,225, Sep. 25, 1991, abandoned, which is a continuation of Ser. No. 451,386, Dec. 15, 1989, abandoned.

[51] Int. Cl.$^6$ .................................................. G01N 33/84
[52] U.S. Cl. .................... 436/79; 436/175; 436/176; 422/61
[58] Field of Search .................... 252/408.1; 422/61, 422/82.09; 436/8, 19, 74–79, 175, 176

[56] References Cited

U.S. PATENT DOCUMENTS

| | | | |
|---|---|---|---|
| 3,934,977 | 1/1976 | Cleaver | 23/230 B |
| 4,383,043 | 5/1983 | Denney et al. | 436/74 |
| 4,454,230 | 6/1984 | Denny | 436/74 |
| 4,503,156 | 3/1985 | Yamazato et al. | 436/79 |

FOREIGN PATENT DOCUMENTS

| | | |
|---|---|---|
| 0075921 | 4/1983 | European Pat. Off. . |
| 0308670 | 3/1989 | European Pat. Off. . |
| 153166P | 9/1983 | Japan ............................ G01N 31/22 |

OTHER PUBLICATIONS

Package Insert–LANCER, Magnesium Rapid Stat diagnostic Kit 1982 Ferguson, et al., Analytical Chemistry, 36:796 (1964).
Package Insert–Roche Magnesium test.
Package Insert–Magensium B–WAKO.
Package Insert–American Monitor Corp.–60 second magnesium.
Clinical Chemistry, vol. 34, No. 6 (1988).
Package Insert–Boeringher, Mannheim–Magnesium.
Youxian, Anal. Chim. Acta, 212:291–295 (1988).
Kaneko et al., Anal. Chem. Acta. 132:165–173 (1981).
Durham et al., "A Survey of the Available Colorimetric Indicators for $Ca^{2+}$ and $Mg^{21}$ Ions in Biological Equipment", Cell Calcium, 4: 47–55 (1983).

*Primary Examiner*—David A. Redding
*Attorney, Agent, or Firm*—George M. Gould; William H. Epstein; Dennis P. Tramaloni

[57] ABSTRACT

The present invention provides novel reagent compositions incorporating chlorophosphonazo III and a chelating agent and methods utilizing such compositions for the determination of magnesium and magnesium concurrently with calcium in an analytical sample as well as diagnostic test kits for such determinations.

13 Claims, No Drawings

METHOD FOR QUANTITATION OF CALCIUM AND MAGNESIUM AND THE NOVEL REAGENT COMPOSITIONS

This is a continuation of application Ser. No. 07/996,361, filed Dec. 23, 1992, now abandoned which is a continuation of Ser. No. 07/765,225, filed Sep. 25, 1991, which is a continuation of Ser. No. 07/451,386, filed Dec. 15, 1989, abandoned.

TECHNICAL FIELD

The invention is directed to a method for quantitating magnesium in an analytical sample as well as a method for quantitating both calcium and magnesium concurrently in an analytical sample as well as the novel reagent compositions used therein.

BACKGROUND OF THE INVENTION

With the exception of potassium, magnesium is the most abundant intracellular ion. It is essential to many physiochemical processes including the activation of ATP in the transfer of energy rich phosphate, the activation of enzymes involved in lipid, carbohydrate, and protein metabolism, and the preservation of the macromolecular structure of DNA, RNA and ribosomes. Magnesium also has a significant influence on the neuromuscular apparatus and decreased concentrations of magnesium may result in tetany and convulsions, while increased levels can cause general anesthesia, respiratory failure and cardiac arrest. Because tetany due to reduced magnesium concentrations is clinically indistinguishable from that caused by low calcium levels it is frequently necessary to perform assays for both serum magnesium and calcium at the same time.

Many methods have been used to determine magnesium levels, including phosphate precipitation techniques, complexometric titration procedures, fluorescent spectrophotometry, and dye absorption methods utilizing Titan yellow. These methods are generally time consuming or suffer from technical drawbacks. The best method for the assay of magnesium is generally considered to be atomic absorption spectrophotometry, however this requires expensive instrumentation which often makes it impracticable for smaller laboratories. The determination of magnesium by reaction with calmagite is also known however with this methodology the reagents are somewhat unstable and the determination in general subject to a variety of interferents.

In general, the existing methodologies for measuring total calcium in biologic fluids involves considerable manipulation of samples and reagents prior to determination. Gravimetric and titrimetric methods usually require large sample volumes. Colorimetric methods, both manual and automated, commonly involve final readings under highly alkaline conditions. The indicators used for such determinations are often unstable at the final pH thus requiring reagent dilution with a strong base. The measurement of calcium and magnesium with chlorophosphonazo III is known, however, the concurrent measurement of both calcium and magnesium with the chlorophosphonazo III methodology requires radical pH changes in order to measure one ion without interference by the other, as well as close control of experimental conditions for reliable results.

SUMMARY OF THE INVENTION

The invention is directed to:

reagent compositions useful in the determination of magnesium in an analytical sample.

reagent compositions useful in the determination of magnesium and calcium concurrently in an analytical sample.

a method for determining magnesium in an analytical sample.

a method for the concurrent determination of calcium and magnesium in an analytical sample.

DETAILED DESCRIPTION

The invention is first directed to reagent compositions useful in the determination of magnesium in an analytical sample. The determination of magnesium according to the instant invention is a two step process. In the first step, a first reagent ("Reagent 1") is added to a sample to be analyzed for magnesium. This Reagent 1 essentially contains a chlorophosphonazo III (CPZ3) and a chelating agent which is selected from a group consisting of EGTA or 1,2-bis(2-aminophenoxy)ethane-N,N,N',N'-tetraacetic acid (BAPTA). Preferably, the chelating agent is ethyleneglycol bis (2-aminoethylether)-N, N, N', N'-tetraacetic acid (EGTA). Reagent 1 should contain from about 0.01 to 1.0 mM CPZ3 and 0.1–100 mM EGTA. The more preferable ranges are 0.05–0.30 mM CPZ3 and 0.1–10 mM EGTA with the most preferred concentration about 0.20 mM CPZ3 and 10 mM EGTA. The Reagent 1 composition may additionally contain one or more buffers, detergents, anti-microbials, or antifoam agents. A suitable buffers are imidazole, Bis-tris propane which is 1,3-(bis[tris(hydroxymethyl)methylamino] propane), monobasic phosphate, tetrabutylammonium hydroxide/boric acid or tris which is (tris[hydroxymethyl] aminomethane). Optimally the imidazole should be at a pH of about 7.6 the Bis-tris propane at a pH of about 8, the monobasic phosphate at a pH of about 7 to 8, tetrabutylammonium hydroxide at a pH of about 7 to 8, and tris at about a pH of 8. A variety of detergents will also suffice including but not limited to cocamidopropylamine oxide (cationic), sodium lauryl ether sulfosuccinate (anionic), octylphenoxypolyethoxyethanol (non-ionic), linear alcohol ethoxylate-sodium (binary anionic/non-ionic), N-alkylbetaine (amphoteric), fluoroalkylalcohol (non-ionic), polypropoxy quaternary ammonium chloride (cationic), cocoamido propyl betaine (amphoteric), oleylamidopropyl betaine (amphoteric), isostearylamidopropyl betaine (amphoteric), capric/ caprylic amidopropyl betaine (amphoteric) and cocoamido betaine, as well as betaines, polyoxyethylene ethers, polyoxyethylene sorbitans, or nonionic fluorosurfactants.

Suitable anti-microbials may be thimerosal, azide, chloramphenicol, methylparaben (methyl p-hydroxybenzoate), propylparaben, n-propyl-p-hydroxy benzoate, 2,4-dichlorobenzylalcohol, gentamycin, or sodiumhydroxymethylamino acetate, as well as trimethoprim and sulfamethoxazole. Suitable anti-foam agents are any silicon based defoaming agents. Reagent 1 preferably contains buffers such as tetrabutylammonium hydroxide, imidazole, and TES; the anti-microbials preferred are sulfamethoxazole and trimethoprim; the detergent preferred is polyoxyethylene sorbitan monolaurate and the anti-foam agent is a silicon based defoaming agent. The function concentration ranges for the nonessential constituents of Reagent 1 are 10–600 mm TES, 0.1–500 mM imidazole, 0.01 to 10% polyoxyethylene sorbitan monolaurate, 1–40% tetrabutylammonium hydroxide, 10–100 microgram per ml sulfamethoxazole, 1–10 microgram per ml trimethoprim and 0.01 to 10% of a silicon based defoaming agent. The preferred ranges are 50–300 mM TES, 0.1–2.0 mM imidazole, 0.1–1% polyoxyethylene sorbitan monolaurate, 1–5% tetrabutylammonium hydroxide, 10–100 µg/ml sulfamethoxazole, 1–10 µg/ml trimethoprim and 0.01–1% of a silicon based defoaming agent. Most preferred is Reagent 1 containing about 3% tetrabutylammonium hydroxide, 50 µg per ml sulfamethoxazole, 145 mM TES, 10 mM EGTA, 1.0 mM imidazole, 0.1% polyoxyethylene sorbitan monolaurate, 5 µg per ml trimethoprim, 0.200 mM CPZ3 and 0.075% of a silicon based defoaming agent.

The second reagent composition which is useful for the measurement of magnesium according to the method of the invention is called Reagent 2. The essential constituent of Reagent 2 is EDTA. Reagent 2 may additionally contain one or more buffers, detergents, anti-microbials, or anti-foam agents similar to those acceptable for Reagent 1. Reagent 2 may range from about 1–500 mM EDTA. However, the range of 10–25 mM is preferred with the best embodiment a concentration of about 16 mM. As with Reagent 1, the preferred buffers are tetrabutylammonium hydroxide, imidazole, and TES; the anti-microbials are sulfamethoxazole and trimethoprim; the detergent is polyoxyethylene sorbitan monolaurate; and the anti-foam agent is a silicon based defoaming agent. Functional concentration ranges of Reagent 2 are 10–600 mM TES, 0.1–500 mM imidazole, 0.01 to 10% polyoxyethylene sorbitan monolaurate, 1–40% tetrabutylammonium hydroxide, 10–100 µg per ml sulfamethoxazole, 1–10 µg per ml trimethoprim and 0.01 to 10% of a silicon based defoaming agent. The more preferred concentration ranges are 50–300 mM TES, 0.1–2.0 mM imidazole, 0.1–1% polyoxyethylene sorbitan monolaurate, 1–5% tetrabutyl ammonium hydroxide, 10–100 µg/ml sulfamethoxazole, 1–10 µg/ml trimethoprim and 0.01–1% of a silicon based defoaming agent. Reagent 2 most preferably contains about 3% tetrabutylammonium hydroxide, 50 µg per ml sulfamethoxazole, 100 mM TES, 16 mM EDTA, 1.0 mM imidazole, 0.1% polyoxyethylene sorbitan monolaurate, 5 µg per ml trimethoprim and 0.075% of a silicon based defoaming agent.

These two novel reagents are used in the determination of magnesium according to the methods of the invention. The invention also covers, however, a method for the concurrent determination of both calcium and magnesium in an analytical sample. This determination requires further novel reagent called Reagent 3, 4 and 5. Reagent 3 is comprised of a CPZ3 and one or more buffers, detergents, anti-microbials or anti-foam agents as set forth for Reagent 1. Preferably in Reagent 3 the buffers are tetrabutylammonium hydroxide, imidazole, and TES; the anti-microbials are sulfamethoxazole and trimethoprim; the detergent is polyoxyethylene sorbitan monolaurate; and the anti-foam agent is a silicon based defoaming agent. Functional concentration ranges of Reagent 3 are about 0.01 to 1.0 mM CPZ3, 10–600 mM TES, 0.1–500 mM imidazole, 0.01–10% polyoxyethylene sorbitan monolaurate, 1–40% tetrabutylammonium hydroxide, 10–100 µg/ml sulfamethoxazole, 1–10 µg per ml trimethoprim and 0.01–10% of a silicon based defoaming agent. More preferably the ranges are 0.05–0.30 CPZ3, 50–300 mM TES, 0.1–2.0 mM imidazole, 0.1–1% polyethoxyethylene sorbitan monolaurate, 1–10% tetrabutylammonium hydroxide, 10–100 µg/ml sulfamethoxazole, 1–10 µg/ml trimethoprim and 0.01–1% of a silicon based defoaming agent. Reagent 3 preferably contains about 3% tetrabutylammonium hydroxide, 50 µg per ml sulfamethoxazole, 145 mM TES, 1.0 mM imidazole, 0.1% polyoxyethylene sorbitan monolaurate, 5 µg per ml trimethoprim, 0.200 mM CPZ3 and 0.075% of a silicon based defoaming agent.

Reagent 4 comprises essentially the same constituents as Reagent 2 and in the same concentration ranges both preferred and functional. The only difference is that in the best mode of Reagent 4 EDTA is substituted with EGTA and the concentration of EGTA is about 60 mM.

Reagent 5 comprises essentially the same constituents as Reagent 2 and in the same concentration ranges both preferred and functional. The only difference is that in the best mode of Reagent 5 the concentration of EDTA is about 32 mM.

The invention is directed to a method for the determination of magnesium in an analytical sample comprising the steps of:

a) mixing sample with a reagent comprised of CPZ3 and a chelating agent selected from the group consisting of EGTA or BAPTA ("Reagent 1"), b) measuring the absorbance of the sample, c) adding a second EDTA containing reagent ("Reagent 2") to the reaction mixture, d) measuring the absorbance of the sample, whereby the difference in absorbance is proportional to the quantity of magnesium in the sample.

An alternate version of the magnesium measurement comprises:

a) mixing sample with a reagent comprised of CPZ3 and a chelating agent selected from the group consisting of EGTA or BAPTA ("Reagent 1"), b) measuring the absorbance of the sample, whereby the difference in absorbance is proportional to the quantity of magnesium in the sample.

Preferably, the chelating agent is EGTA. Any analytical sample is suitable such as serum, plasma or urine however any other analytical sample is suitable, for example water samples for testing the concentrations of analyte in public water. As a preferred embodiment of the method concentrations of both Reagents 1 and 2 are as set forth above. When serum or plasma is used, the blood may be collected in serum tubes or tubes with anticoagulant such as heparin, sodium fluoride, or oxalate. The absorbance during each step of the procedure may be measured at a wavelength which is sensitive to magnesium binding preferably either 550 or 675 nanometers (nm). If the absorbance is read at 550 nm, then the quantity of magnesium in the sample is determined by the absorbance decrease at 550 nm when the magnesium in the sample complexes with CPZ3. If, on the other hand, the absorbance is read at 675 nm, the absorbance increases as the sample magnesium complexes with CPZ3. Either absorbance reading is possible although 675 nm is preferred. The difference in absorbance is proportional to the quantity of magnesium in the sample. The EDTA in Reagent 2 binds magnesium and gives a blank for the sample-reagent mixture. The blank reduces interference from substances at the measuring wavelength such as triglycerides, hemoglobin, and biltrubin. To obtain optimal results the pH for the CPZ3 reagent should be about pH 7.5. This allows for increased reagent stability. For example in the old calmagite methods for measuring magnesium a pH range of 10–13 was required, which in turn created reagent instability. The neutral pH for the CPZ3 containing reagent of the invention virtually eliminates $CO_2$ absorption and reagent instability when the reagent remains exposed to open air for any length of time. TES buffer is the preferred buffer for use in the reagents because of a pKa of 7.5, and the EGTA in Reagent 1 eliminates interference from sample calcium. The silicon based defoaming is added to both reagents to reduce bubbling from the detergent. Other bases can be used instead of tetrabutylammonium hydroxide, for example as NaOH or KOH.

The assay of the invention may be conducted on standard laboratory analytical instruments such as the COBAS BIO®, COBAS FARA™, or COBAS MIRA™, (Hoffmann-La Roche Inc., Nutley, N.J.).

On the COBAS MIRA 100 to 270 µl Reagent 1 is mixed with 2 to 95 µl sample in the first cycle. The absorbance is read at 550 nm. Then 30 to 90 µl Reagent 2 is added and after 0.5 to 3 minutes (cycle 8) a second absorbance reading made at 550 nm. Preferably, however, 180 µl of Reagent 1 is mixed with a 4.5 µl sample in the first cycle. The absorbance is read at 550 nm. Sixty µl of Reagent 2 is added and after 3 minutes (cycle 8) a second absorbance reading is made at 550 nm. The absorbance change is proportional to the concentration of magnesium in the sample. Standards and controls are run in conjunction with the samples and the magnesium concentration in the samples is calculated from the standard curve in the usual manner.

The magnesium method of the invention may also be determined on the COBAS FARA or COBAS B10. In this instance 30 to 225 µl Reagent 1 is mixed with 2 to 95 µl sample, incubated for 5 to 1000 seconds at 20°–40° C. and the absorbance read at 675 nm. Then 10 to 75 µl Reagent 2 is added and after 0.5 to 1000 seconds a second absorbance reading is taken at 675 nm. Preferably 180 µl Reagent 1 is mixed with 2 µl of sample. The assay is run at 37° and after mixing Reagent 1 with sample, the mixture incubated for 120 seconds after which the absorbance is read at 675 nm. Then 60 µl Reagent 2 is added and after 100 seconds a second absorbance reading is made at 675 nm. The absorbance difference between the two readings is proportional to the concentration of magnesium in the sample.

The invention is also directed to a method for the concurrent determination for both calcium and magnesium and in an analytical sample comprising the steps of:

a) mixing a sample with Reagent 3, b) measuring the absorbance of the sample, c) adding Reagent 4, d) measuring the absorbance of the sample, e) adding Reagent 5, f) measuring the absorbance of the sample whereby the difference in absorbance between (d) and (b) is proportional to the quantity of calcium in the sample and the difference in absorbance between (f) and (d) is proportional to the quantity of magnesium in the sample.

As above, the analytical sample may be serum, plasma, urine or any other body fluids as well as water or other samples. The absorbance may be measured at 550 nm or 675 nm. Preferably, the concentrations of Reagents 3, 4 and 5 are as mentioned previously.

In this method the assay may also be conducted on the COBAS BIO, COBAS MIRA, or COBAS FARA. For example, on the COBAS FARA the assay is run at 37° C. Approximately 30 to 225 µl Reagent 3 is mixed with 2 to 95 µl sample and the absorbance read at 675 nm. Then 5–40 µl of Reagent 4 is added and the absorbance is read. Then 5 to 40 µl of Reagent 5 is added and the absorbance read. Most optimally about 180 µl Reagent 3 is mixed with 2 µl sample and the absorbance read at 675 nm. Then 30 µl Reagent 4 is added and the absorbance read. Then 30 µl Reagent 5 is added and the absorbance read. The calcium concentration is calculated from the absorbance change between the first two reads and the magnesium concentration between reads 2 and 3.

It is also possible to substitute the compound 8-hydroxyquinoline for EGTA Reagent 4. In this case $µg^{2+}$ is first measured by the absorbance difference between (d) and (b). The difference of absorbance between (f) and (d) would be proportional to the calcium in the sample.

The present invention will be fully described in connection with the following examples which are set forth for the purposes of illustration only.

EXAMPLE 1

Reagent Preparation

Reagent 1 (1 liter): 75 mL tetrabutylammonium hydroxide and 0.050 g sulfamethoxazole are dissolved in about 750 mL of deionized water. The final components are fully dissolved in the reagent solution in the following order: first, 33.3 g TES (free acid); second, 3.92 g EGTA (free acid); third 0.0681 g imidazole; fourth 0.0050 g trimethoprim; fifth 0.1515 g Chlorophosphonazo III. Finally, 1.0 g polyoxyethylene sorbitan monolaurate (TWEEN 20) and 0.75 g of a silicon based defoaming agent (Foamaster FLD) are added, the pH adjusted to 7.5 with HCl and the volume brought to 1 liter. The concentrations of the components in Reagent 1 are:

3% tetrabutylammonium hydroxide 145 mM TES (free acid)

10 mM EGTA (free acid)

1.0 mM imidazole

5 µg/mL trimethoprim 0.20 mM Chlorophosphonazo III 0.1% TWEEN 20

0.075% Foamaster FLD

50 µg/ml sulfamethoxazole

Reagent 2 (1 liter): 75 mL tetrabutylammonium hydroxide and 0.050 g sulfamethoxazole are dissolved in about 750 mL deionized water. The final components are fully dissolved in the reagent solution in the following order: first 22.9 g TES free acid; second, 4.72 g EDTA free acid; third, 0.0681 g imidazole, fourth 0.0050 g trimethoprim. Finally 1.0 g TWEEN 20 and 0.75 g Foamaster FLD are added, the pH adjusted to 7.5 with HCl and the volume brought to 1 liter. The final concentrations of the components in Reagent 2 are:

3% tetrabutylammonium hydroxide
100 mM TES (free acid)
16 mM EDTA (free acid)
1.0 mM imidazole
50 µg/mL sulfamethoxazole
5 µg/mL trimethoprim
0.1% TWEEN 20
0.075% Foamaster FLD.

EXAMPLE 2

Magnesium Determination on the COBAS MIRA

The assay is conducted at 37° C. and 180 µL of Reagent 1 is mixed with 4.5 µl sample in the first cycle. The absorbance is read at 550 nm. 60 mL Reagent 2 is added in the second cycle and after 3 minutes (cycle 8) a second absorbance reading is taken at 550 nm. The absorbance change between the 2 readings is proportional to the concentration of magnesium in the sample. Standards and controls are run in conjunction with the samples and the magnesium concentration in the samples is calculated from the standard curve in the usual manner.

The following table illustrates the absorbance changes when magnesium is determined according to the method of the invention:

| Sample | $A_{550}$ Cycle 1 | $A_{550}$ Cycle 8 | Δ (Cycle 8 − Cycle 1) |
|---|---|---|---|
| 0.49 mmol/L µg++ | 1.7079 | 1.7737 | 0.0658 |
| 0.85 | 1.6500 | 1.7524 | 0.1024 |
| 1.07 | 1.6386 | 1.7645 | 0.1259 |
| 1.32 | 1.6096 | 1.7604 | 0.1508 |
| 1.52 | 1.5772 | 1.7483 | 0.1711 |

EXAMPLE 3

Magnesium Determination on the COBAS FARA

The assay is conducted at 37° C. and 180 mL of Reagent 1 is mixed with 2 µL sample, incubated for 120 seconds and the absorbance read at 675 nm. 60 µL Reagent 2 is added and after 100 seconds a second absorbance reading is taken at 675 nm. The absorbance change between the two readings is proportional to the magnesium concentration of the sample. Standards and controls are run in conjunction with the samples and the magnesium concentration of the samples is calculated from the standard curve in the usual manner.

The table illustrates the absorbance changes when magnesium is determined according to the method of the invention:

| Sample | $A_{675}$ (120 seconds) | $A_{675}$ (220 seconds) | ΔA (120 seconds − 220 seconds) |
|---|---|---|---|
| 0.42 mmol/L Mg++ | 1.5310 | 1.2477 | 0.2833 |
| 0.88 | 1.6698 | 1.2622 | 0.4076 |
| 1.32 | 1.8039 | 1.2787 | 0.5252 |
| 1.73 | 1.9118 | 1.2760 | 0.6358 |
| 2.11 | 2.0399 | 1.2859 | 0.7540 |

EXAMPLE 4

Correlation with Prior Art

Serum samples from ninety-four random patients were assayed on the COBAS MIRA according to the method of Example 2, as well as the, Sigma Calmagite Magnesium method (test kit Cat. No. 595-m). 240 µL reagent (prepared by combining equal parts of Reagents 1 and 2) was pipetted into cuvette and an absorbance reading taken at 550 nm. 2.4 µL sample is then added, and after 1 minute a second absorbance reading is taken at 550 nm. The change in absorbance between the two readings correlates with the magnesium concentration in the sample. The samples assayed according to Example 2 were correlated with the same samples assayed according to the Sigma Calmagite Method. A linear regression line where Y=1.08 X−0.14 resulted where Y is the sample value determined by the assay method of the invention and X is the sample value determined by the prior art Calmagite method. The coefficient of correlation between these two methods is 0.9544.

EXAMPLE 5

Determination of Calcium and Magnesium on COBAS FARA

The assay is conducted at 37° C. and 180 µL Reagent 3 is mixed with 2 µL sample and the absorbance is read at 675 nm. 30 µL of Reagent 4 is added and the absorbance is read at 675 nm. 30 µL of Reagent 5 is added and absorbance reads at 675 nm. The calcium concentration is calculated from the absorbance change between reads (1) and (2) and the magnesium concentration is calculated from the absorbance difference between read (2) and read (3).

Reagent 3 (1 liter): 75 ml tetrabutylammonuim hydroxide and 0.050 g sulfamethoxazole are dissolved in approximately 750 mL deionized water. The final components are fully dissolved in the reagent: 33.3 g TES free acid, 0.0681 g imidazole; 0.0050 g trimethoprim, and 0.1515 g CPZ3. Finally, 1.0 g TWEEN 20 and 0.75 g Foamaster FLD are added. The pH is adjusted to 7.5 with HCl and the volume brought to 1 liter. The concentrations of the components in Reagent 3 are:

3% tetrabutylammonium hydroxide
50 µg/mL sulfamethoxazole
145 mM TES free acid
1.0 mM imidazole 5 µg/mL trimethoprim 0.20 mM ChlorophosphonazoIII 0.1% TWEEN 20

0.075% Foamaster FLD

Reagent 4: Reagent 4 is made in the same manner as Reagent 2 resulting in the following component concentrations:

3% tetrabutylammonium hydroxide

5 µg/mL trimethoprim

50 µg/mL sulfamethoxazole 100 mM TES free acid 1.0 mM imidazole 60 mM EGTA free acid 0.1% TWEEN 20

0.075% Foamaster FLD pH 7.5

Reagent 5: Reagent 5 is made in the same manner as Reagent 2 resulting in the following component concentrations:

3% tetrabutylammonium hydroxide

5 µg/mL trimethoprim

50 µg/mL sulfamethoxazole 100 mM TES free acid 1.0 mM imidazole 32 mM EDTA free acid 0.1% TWEEN 20

0.075% Foamaster FLD pH 7.5

EXAMPLE 7

Calcium Interference

The assays are conducted as described in Examples 2 and 3. A single serum sample was aliquoted into a number of samples and varying amounts of calcium were added to each aliquot as set forth below. The EGTA in Reagent 1 acts to chelate the calcium thus minimizing its interference in the magnesium assay.

The table below illustrates the minimal interference from calcium.

| Calcium added to Sample | Magnesium Value Determined in Ex. 2 (mmoL/L) | Magnesium Value Determined in Ex. 3 (mmoL/L) |
| --- | --- | --- |
| 0 mg/dL | 0.75 | 0.77 |
| +5 mg/dL | 0.74 | 0.77 |
| +10 mg/dL | 0.76 | 0.78 |
| +15 mg/dL | 0.78 | 0.80 |
| +20 mg/dL | 0.78 | 0.80 |
| +30 mg/dL | 0.79 | 0.78 |

EXAMPLE 8

Stability of Reagents 1 and 2 at Elevated Temperatures

There is no change in performance of Reagents 1 and 2 after storage at 55° C. for 3 months. The table below illustrates the performance of stressed reagents (stored at 55° C. for 3 months) compared to fresh reagent. (Serum samples assayed according to Example 3).

| Control Reagent (Fresh) | Stressed Reagent |
| --- | --- |
| 0.48 | 0.47 |
| 1.39 | 1.38 |
| 2.25 | 2.21 |

EXAMPLE 9

Correlation with Atomic Absorption Spectrophotometry

Atomic absorption spectrophotometry (AA) is a well known method used for magnesium determination. Eighty-four patient serum samples were analyzed for calcium by AA by Roche Biomedical Labs, Raritan, N.J., according to Tietz, Clinical Chemistry (1986). The same samples were analyzed for calcium according to the method set forth in Example 2 and 3 herein. The results are as follows:

| Methods | Linear Regression Line | Coefficieny of Correlation (r) |
| --- | --- | --- |
| Example 2 MIRA(y) v AA(x) | y = 1.06 x −.07 | 0.9405 |
| Example 3 FARA(y) v AA(x) | y = 1.04 x −.02 | 0.9496 |

As evidenced by the above, the correlation between AA and the methods of the invention are 0.9405 and 0.9496.

EXAMPLE 10

Example of Single Reagent Application

Reagent 2 provides a sample blank for the assay but the assay still performs without Reagent 2.

| Assay on MIRA: | |
| --- | --- |
| 100–600 µL | 2–95 µL |

180 µL of Reagent 1 is mixed with 4.5 µL sample and absorbance is measured at 550 nm. This absorbance is substracted from a water blank and the absorbance charge is proportioned to the sample magnesium concentration

| SAMPLE | Asso. | ΔA (blank − sample) |
| --- | --- | --- |
| BLANK | 1.7768 | |
| 0.49 mmol/L Mg | 1.7079 | .0689 |

-continued

| SAMPLE | Asso. | ΔA (blank − sample) |
|---|---|---|
| 0.85 | 1.6500 | 0.1268 |
| 1.07 | 1.6386 | 0.1382 |
| 1.32 | 1.6096 | 0.1672 |
| 1.52 | 1.5772 | 0.1996 |
| Assay on FARA: | | |
| (0–370 μL | | 1–95 μL |

180 μL of Reagent 1 is mixed with 2 μL of sample and absorbance is measured at 675 nm. The absorbance from a water blank is substracted from sample absorbance and this change in absorbance is proportional to the sample magnesium concentration.

| SAMPLE | $A_{675}$ | ΔA (sample − blank) |
|---|---|---|
| BLANK | 1.3762 | |
| 0.42 mmol/L $Mg^{++}$ | 1.5310 | 0.1548 |
| 0.88 | 1.6698 | 0.2936 |
| 1.32 | 1.8039 | 0.4277 |
| 1.73 | 1.9118 | 0.5356 |
| 2.11 | 2.0399 | 0.6637 |

I claim:

1. A method for the determination of magnesium in an analytical sample comprising the steps of:
   a. mixing the sample with a first reagent comprised of chlorophosphonazo III ("CPZ3") and a chelating agent selected from the group consisting of ethyleneglycol bis (2-aminoethylether)-N,N,N',N'-tetracetic acid ("EGTA") and 1,2 bis (2-aminophenoxy) ethane-N,N,N',N'-tetracetic acid ("BAPTA") ("Reagent 1"),
   b. measuring the absorbance of the sample,
   c. adding a second reagent comprising EDTA ("Reagent 2") to the reaction mixture,
   d. measuring the absorbance of the sample,
whereby the difference in absorbance is proportional to the quantity of magnesium in the sample.

2. The method of claim 1 wherein the chelating agent is EGTA.

3. The method of claim 2 where the analytical sample is serum, plasma, or urine.

4. The method of claim 3 wherein the absorbance is read at 550 nm or 675 nm.

5. The method of claim 4 wherein 100 to 270 μl of the first reagent is mixed with 2 to 95 μl sample in step a) and the absorbance read at 550 nm, after which 30 to 90 μl of the second reagent is added and after 0.5 to 3 minutes a second absorbance reading made at 550 nm.

6. The method of claim 5, wherein 180 μl of the first reagent is mixed with 4.5 μl sample and the absorbance read at 550 nm; after which 60 μl of the second reagent is added and after about 3 minutes the absorbance is read at 550 nm.

7. A method for the determination of calcium and magnesium in an analytical sample comprising the steps of:
   a. mixing a sample with a reagent comprising chlorophosphonazo III ("Reagent 3"),
   b. measuring the absorbance of the sample,
   c. adding a reagent comprising ethyleneglycol bis (2-aminoethylether)-N,N,N',N'-tetracetic acid-("Reagent 4"),
   d. measuring the absorbance of the sample,
   e. adding a reagent comprising EDTA ("Reagent 5"),
   d. measuring the absorbance of the sample,
whereby the difference in absorbance between step (d) and step (b) is proportional to the quantity of calcium in the sample and the difference between step (f) and step (d) is proportional to the quantity of magnesium in the sample.

8. The method of claim 7 wherein the analytical sample is serum, plasma, or urine.

9. The method of claim 8 wherein the absorbance is measured at 550 nm or 675 nm.

10. The method of claim 9 wherein 30 to 225 μl Reagent 3 is mixed with 2 to 95 μl sample and the absorbance read at 675 nm, after which 5 to 40 μl Reagent 4 is added and the absorbance read at 675 nm, after which 5 to 40 μl Reagent 5 is added and the absorbance read at 675 nm.

11. The method of claim 10 wherein about 180 μl Reagent 3 is mixed with 2 μl sample and the absorbance read at 675 nm, after which 30 μl Reagent 4 is added and the absorbance read at 675 nm, after which 30 μl Reagent 5 is added and the absorbance read at 675 nm.

12. A diagnostic test kit useful for the measurement of calcium in an analytical sample comprising:
   a. a container of a reagent composition comprised of chlorophosphonazo III and a chelating agent consisting of ethyleneglycol bis (2-aminoethylether)-N,N,N',N'-tetracetic acid or 1,2 bis (2-aminophenoxy) ethane-N,N,N',N'-tetracetic acid, and
   b. a container of a reagent composition comprised of EDTA.

13. A diagnostic test kit useful for the measurement of calcium and magnesium in an analytical sample comprising:
   a. a container of a reagent composition comprised of chlorophosphonazo III,
   b. a container of a reagent composition comprised of ethyleneglycol bis (2-aminoethylether)-N,N,N',N'-tetracetic acid, and
   c. a container of a reagent composition comprised of EDTA.

* * * * *